（12）United States Patent
Imamura et al.

(10) Patent No.: US 12,130,270 B2
(45) Date of Patent: Oct. 29, 2024

(54) HUMIDIFICATION TYPE HIGHLY-SENSITIVE/HIGHLY-SELECTIVE AMMONIA DETECTION METHOD AND DETECTION DEVICE USING NANOMECHANICAL SENSOR

(71) Applicant: NATIONAL INSTITUTE FOR MATERIALS SCIENCE, Ibaraki (JP)

(72) Inventors: Gaku Imamura, Ibaraki (JP); Kosuke Minami, Ibaraki (JP); Kota Shiba, Ibaraki (JP); Genki Yoshikawa, Ibaraki (JP)

(73) Assignee: NATIONAL INSTITUTE FOR MATERIALS SCIENCE, Ibaraki (JP)

( * ) Notice: Subject to any disclaimer, the term of this patent is extended or adjusted under 35 U.S.C. 154(b) by 328 days.

(21) Appl. No.: 17/619,024

(22) PCT Filed: May 8, 2020

(86) PCT No.: PCT/JP2020/018649
§ 371 (c)(1),
(2) Date: Dec. 14, 2021

(87) PCT Pub. No.: WO2020/255580
PCT Pub. Date: Dec. 24, 2020

(65) Prior Publication Data
US 2022/0291185 A1    Sep. 15, 2022

(30) Foreign Application Priority Data

Jun. 18, 2019  (JP) .................................. 2019-112434

(51) Int. Cl.
*G01N 33/00* (2006.01)
*C08F 222/06* (2006.01)
(Continued)

(52) U.S. Cl.
CPC ....... *G01N 33/0054* (2013.01); *C08F 222/06* (2013.01); *G01L 1/18* (2013.01);
(Continued)

(58) Field of Classification Search
CPC ..... C08F 222/06; G01L 1/18; G01N 33/0054; G01N 5/02; G01N 29/022; G01N 2291/0256
See application file for complete search history.

(56) References Cited

U.S. PATENT DOCUMENTS 3,630,956 A * 12/1971 Benning ............ H01M 8/04119
                                                    252/372
6,123,324 A *  9/2000 Swan ...................... B01F 23/12
                                                    261/78.2
(Continued)

FOREIGN PATENT DOCUMENTS

CN      107870183        4/2018
JP      2016-128776      7/2016
(Continued)

OTHER PUBLICATIONS

International Search Report issued Jun. 23, 2020 in International (PCT) Application No. PCT/JP2020/018649.
(Continued)

*Primary Examiner* — Kristina M Deherrera
*Assistant Examiner* — Jean F Morello
(74) *Attorney, Agent, or Firm* — Wenderoth, Lind & Ponack, L.L.P.

(57) ABSTRACT

An object of the present invention is to detect ammonia with high sensitivity and high selectivity using a nanomechanical sensor with a structure that is as simple as possible. A method for detecting ammonia according to an embodiment of the present invention comprises supplying a sample gas possibly containing ammonia to a nanomechanical sensor
(Continued)

that detects a stress or a displacement using poly(methyl vinyl ether-alt-maleic anhydride) as a material of a receptor layer, and detecting presence or absence of ammonia or a content of ammonia in the sample gas based on an output signal from the nanomechanical sensor, in which the sample gas is a humidified sample gas with controlled relative humidity.

7 Claims, 4 Drawing Sheets

(51) Int. Cl.
  *G01L 1/18* (2006.01)
  *G01N 5/02* (2006.01)
  *G01N 29/02* (2006.01)
(52) U.S. Cl.
  CPC .............. *G01N 5/02* (2013.01); *G01N 29/022* (2013.01); *G01N 2291/0256* (2013.01)

(56) References Cited

U.S. PATENT DOCUMENTS

| | | | |
|---|---|---|---|
| 2005/0279987 A1 | 12/2005 | Star et al. | |
| 2008/0093226 A1* | 4/2008 | Briman .............. | G01N 33/0062 204/406 |
| 2013/0133433 A1 | 5/2013 | Yoshikawa et al. | |
| 2018/0088088 A1 | 3/2018 | Shimomai et al. | |
| 2020/0249201 A1 | 8/2020 | Shiba et al. | |

FOREIGN PATENT DOCUMENTS

| | | |
|---|---|---|
| WO | 2008/052104 | 5/2008 |
| WO | 2011/148774 | 12/2011 |
| WO | 2018/221283 | 12/2018 |

OTHER PUBLICATIONS

Yoshikawa, Genki et al., "Nanomechanical Membrane-type Surface Stress Sensor", NANO Letters 11, 2011, pp. 1044-1048.
Ding, Bin et al., "Electrospun fibrous polyacrylic acid membrane-based gas sensors", Sensors and Actuators B 106, 2005, pp. 477-483.
Seung-Woo, Lee et al., "Volatile Biomarker Analysis and Advanced Gas-sensing Instruments", 2018, p. 189 (with machine translation).
Tsuboi, Osamu et al., "Mobile Sensor that Quickly and Selectively Measures Ammonia Gas Components in Breath", FUJITSU 68, 2017, pp. 59-64 (with machine translation).
Ikeda, Shiro et al., "Measurement of Trace Gases Emitted from Human Skin Using a Passive Indicator", Kanagawa Prefecture Manufacturing Technology Exchange Meeting 2014 abstracts, p. 3101 (with machine translation).
TIPO Examination Report issued Sep. 5, 2022 in corresponding Taiwanese Patent Application No. 109115981, with English language translation.
Notice of Reasons for Refusal issued Nov. 29, 2022 in corresponding Japanese Patent Application No. 2021-527442, with English language translation.
Extended European Search Report issued May 25, 2023 in corresponding European Patent Application No. 20827748.3.
Communication pursuant to Article 94(3) EPC issued Dec. 22, 2023 in corresponding European Patent Application No. 20827748.3.

* cited by examiner

HUMIDIFICATION TYPE HIGHLY-SENSITIVE/HIGHLY-SELECTIVE AMMONIA DETECTION METHOD AND DETECTION DEVICE USING NANOMECHANICAL SENSOR

TECHNICAL FIELD

The present invention relates to a humidification type highly-sensitive/highly-selective ammonia detection method and detection device using a nanomechanical sensor.

BACKGROUND ART

In recent years, a nanomechanical sensor that detects a minute change in some physical quantity on or near a surface of a sensor body, has progressed, and thereby, it has become possible to easily detect a trace component in a given sample. Note that, in the present specification, the "nanomechanical sensor" refers to a sensor that detects a stress generated by adsorption or absorption of an object to be detected by a so-called receptor layer coating a sensor surface or a displacement (mechanical deformation or deflection) caused as a result of the stress. As the nanomechanical sensor, various principles and structures have been proposed. In particular, a Membrane-type Surface stress Sensor (MSS) (Patent Literature 1 and Non Patent Literature 1) that has been filed for patent and disclosed by the present inventors has characteristics that are easily used for various applications, such as high sensitivity and stability of operation.

When a chemical substance (hereinafter, a chemical substance to be detected may be referred to as a "specimen") is supplied to the nanomechanical sensor, the minute change in physical quantity is caused by interaction with the specimen. However, since most of specimens do not adsorb or act in a like manner in a large amount onto a surface of a nanomechanical sensor body itself, only an almost undetectable change in physical quantity is caused. Therefore, in most cases, a material that incorporates a desired specimen as much as possible by adsorption, reaction, or the like, and causes a large change in physical quantity as much as possible by such incorporation is selected, and the material is fixed in some form, for example in a form in which the material is applied to a surface of the sensor body. A substance that causes a change in physical quantity detectable by the sensor body by being fixed onto the surface of the sensor body and a film thereof are referred to as a receptor and a receptor layer (in some cases, also referred to as a sensitive material and a sensitive film), respectively.

One of promising application fields of the nanomechanical sensor is, but not particularly limited to, analysis of a sample released from a living body to the outside of the body by respiration, sweating, excretion, or the like, or a sample taken out from the inside of a living body such as blood or various other body fluids, wherein the analysis includes confirmation of presence of a target substance, quantitative determination thereof, determination as to whether or not the amount thereof exceeds a certain threshold, and the like. By such analysis, it is possible to determine a health condition of an animal such as a human or livestock (and a plant in some cases), to diagnose a disease, and the like. In addition to such determination and diagnosis, various applications using detection of a component contained in this kind of sample or diverged therefrom by evaporation or the like are conceivable.

In particular, in recent years, there is an increasing need for detecting ammonia in a sample. Ammonia in a body is mainly generated by decomposition of a protein, movement of muscles, and the like, and most of the ammonia is metabolized to urea by a urea cycle in the liver and is excreted from the kidney into urine. Therefore, when an abnormality (for example, liver cirrhosis or hepatic encephalopathy) occurs in an organ involved in these metabolic cycles, an ammonia concentration in blood increases, and an ammonia concentration in exhaled breath also increases due to gas exchange in the alveoli in the lung (B. Timmer et al., Sens. Actuators B, 107, 666 (2005), B. J. C. Mutch, E. W. Banister, Medicine & Science in Sports & Exercise, 15 (1): 41-50 (1983), J P Ong, A Aggarwal, D Krieger, et al., American Journal of Medicine, 114, 188-193 (2003)). It has also been reported that the concentration of ammonia contained in a skin gas increases due to physical or mental fatigue (Shota Furukawa et al., 2015 Indoor Environment Society Academic Meeting Summary, 198-199 (2015)). Therefore, if presence or absence of ammonia or the content of ammonia can be detected with high sensitivity, a human health condition may be monitored based on the ammonia concentration.

Spanel et al, report that a median value of an ammonia concentration in exhaled breath sampled from subjects aged 20 to 60 years is 833 ppb (0.833 ppm) (P. Spanel et al. J. Breath Res. 1 (2007)). On the other hand, since a limit value that can be perceived by a human is said to be 55 ppm, sensory evaluation by human's olfactory sense is difficult except for a case where a disease state is particularly severe. Therefore, in order to monitor a health condition, a sensor capable of detecting ammonia having a low concentration of 1 ppm or less is required.

In addition, with recent progress in MEMS technology, a gas sensor with small size and low power consumption has appeared. In addition, with progress of ICT technology, IoT in which various devices are connected to the Internet to exchange information with each other is rapidly progressing. Therefore, if an ammonia concentration in a skin gas or exhaled breath can be measured, application as a wearable device that monitors a human health condition based on the ammonia concentration is also expected.

CITATION LIST

Patent Literature

Patent Literature 1: WO 2011/148774 A
Patent Literature 2: JP 2016-128776 A
Patent Literature 3: WO 2018/221283 A

Non Patent Literature

Non Patent Literature 1: G. Yoshikawa, T. Akiyama, S. Gautsch, P. Vettiger, and H. Rohrer, "Nanomechanical Membrane-type Surface Stress Sensor" Nano Letters 11, 1044-1048 (2011).

Non Patent Literature 2: B. Ding et al., Sens. Actuators B 106, 477 (2005).

Non Patent Literature 3: Lee Seung-woo, Volatile Biomarker Analysis and Advanced Gas-sensing Instruments, p. 189 (2018).

Non Patent Literature 4: Shu Tsuboi et al., FUJITSU 68, 59 (2017).

Non Patent Literature 5: Shiro Ikeda et al., Kanagawa Prefecture Manufacturing Technology Exchange Meeting 2014 abstracts, 3101 (2014).

SUMMARY OF INVENTION

Technical Problem

As a conventional ammonia detection sensor, for example, it has been proposed that, in an ammonia detection element that detects ammonia in exhaled breath, an element part is composed of a sensitive part containing a solid superacid substance having a Hammet acidity function $H_0$ of −11.93 or less as a main component, and a zeolite layer (surface layer) covering the sensitive part (Patent Literature 2).

However, the ammonia sensor of Patent Literature 2 applies an AC voltage to electrodes, and detects an ammonia concentration based on a change in impedance (Z) of the sensitive layer or the surface layer measured from a current value flowing between both electrodes. At the time of operation, it is necessary to heat the element part to a high temperature of 300° C. or higher using a heating means such as a heater. In addition, when the sensor is repeatedly used, similarly, it is necessary to perform cleaning by heating the element part to a high temperature of about 600° C. Note that an oxide semiconductor gas sensor using $SnO_2$ or the like mentioned in Patent Literature 2 also requires heating during operation. Therefore, these ammonia detection sensors do not meet requirement of small size and low power consumption.

Furthermore, in Patent Literature 2, by adopting the above configuration, even ammonia having a low concentration of about 1 ppm (for example, 100 ppb (0.1 ppm) to 5 ppm) such as ammonia in exhaled breath can be detected with high accuracy. However, since the sensor of Patent Literature 2 has sensitivity also to a basic gas other than ammonia only with the sensitive layer, a filter that selectively transmits ammonia is required, and as a result, a manufacturing process and a structure are complicated. Therefore, a sensor having both high sensitivity and high selectivity to ammonia with a structure as simple as possible is desired.

As ammonia detection using a polymer as a sensitive film, polyacrylic acid (PAA) is most widely used (Non Patent Literature 2). PAA is a polymer having a repeating structure of carboxyl groups, and is known to exhibit high reactivity to water and ammonia. Lee et al, have reported highly sensitive ammonia detection with a detection limit of 0.72 ppm in a high humidity environment (relative humidity (RH) of about 65%) using a sensor in which an alternately stacked film of poly(allylamine hydrochloride) (PAH) and silica nanoparticles ($SiO_2$) is formed on a surface of a quartz crystal microbalance (QCM) and PAA is introduced into the film to form a sensitive film (Non Patent Literature 3). In Non Patent Literature 3, very high sensitivity has been achieved by using a QCM that does not require heating, and it can be said to be an important result. However, particularly for detection of ammonia contained in exhaled breath or a skin gas, higher sensitivity is desired. In addition, in an experiment of Non Patent Literature 3, measurement is performed at a relatively large flow rate of 0.4 L/min, but in order to reduce a burden in collecting exhaled breath or a skin gas, measurement with a smaller amount of gas is preferable. Furthermore, the alternately stacked film is required when a sensor is manufactured, and a sensor that can be manufactured more simply and inexpensively is required.

Examples of highly sensitive ammonia detection using a special material as a sensitive film include a sensor using copper bromide (CuBr) by Tsuboi et al. (Non Patent Literature 4). This uses a property that a monovalent copper ion is easily coordinately bonded to an ammonia molecule to form a complex, and many studies have been performed heretofore (M. Bendahan et al. Sens. and Actuators B, 84, 6 (2002), Y. Zheng et al. J. Phys. Chem. C 115, 2014, (2011)). As an alternative to a conventional method, Tsuboi et al. have developed a method for brominating a Cu thin film using a methanol solution of $CuBr_2$, and have succeeded in manufacturing a sensor capable of detecting even ammonia having a concentration of 100 ppb (0.1 ppm). This not only achieves a sensitivity at a level that can be used for measurement of exhaled breath or a skin gas, but also makes quantification of an ammonia concentration possible even from an initial response of about 10 seconds because the ammonia concentration and an electric resistance change that is a signal from the sensor have a linear relationship. Meanwhile, also in this demonstration experiment, a relatively large flow rate (1 L/min, 4 L/min, or the like) is used, and it is desired to perform demonstration at a low flow rate. In addition, in a sensor device manufactured by way of trial, for example, it is necessary to dispose a drying chamber in which a slaked lime drying agent is put in a front stage of a measurement chamber to adjust relative humidity to about 40%, and stable measurement in a high humidity environment is desired.

In addition, application of a passive indicator is expected as a simple method for measuring ammonia in a skin gas (Non Patent Literature 5). This is a device to which a passive flux sampler (S. Furukawa, Y. Sekine et al., J. Chromatogr. B 1053, 60 (2017)) developed by Furukawa, Sekine, and the like is applied, and is a device which has a structure in which a color reagent is fixed to a collection part (solid phase), and passively collects a target component in air using the principle of molecular diffusion. The emission amount of a target component gas is examined from a change in color caused by exposure to a gas containing a target substance such as ammonia for a long time. This passive indicator makes extremely simple measurement possible, and by applying more than 600 kinds of gas detection tube techniques, further versatility, higher performance, and the like are expected. Meanwhile, in this method, it is necessary to recognize a color change (colorimetric recognition), and a spectrophotometer or the like is required for accurate quantification. In addition, the passive indicator incorporates a moisture removing agent in which a hygroscopic powder such as silica gel is carried on a nonwoven fabric, and it is desired to cope with further simple measurement in a high-humidity environment.

Solution to Problem

By using a nanomechanical sensor (particularly a sensor that operates in a static mode in which an element is not resonated and has an electric reading system, for example, a surface stress sensor), it is possible to largely reduce size and power consumption of a measurement system. However, in analysis using the nanomechanical sensor, it may be difficult to detect a specimen due to moisture contained in a sample. Not limited to a sample obtained from a living body such as exhaled breath or a skin gas, a large amount of water exists in nature, and water is used in many activities in daily life and industry. Therefore, moisture is contained in a sample at a high rate in extremely many aspects. When such a sample is analyzed by the nanomechanical sensor, a receptor absorbs water contained in the sample, and a large part of a change in physical quantity such as surface stress generated in a receptor layer is based on the absorbed water. As a result of studies by the present inventors, it has been confirmed that, when a large amount of water is absorbed by a receptor, a phenomenon called a kind of masking that affects a change in physical quantity by another trace component may occur because, for example, a change in physical quantity such as a surface stress of a receptor is saturated, adsorption of another trace component to the receptor is inhibited even if the change is not saturated, or a change in a physical quantity by water and a change in physical quantity by another component are not necessarily linearly superimposed. That is, most of detection signals based on a change in stress are components derived from water, and a signal component due to a trace component is shielded by the component derived from water, which may make it difficult to detect a specimen.

Therefore, in general, it is intended to reduce a negative influence that moisture contained in a sample can have on measurement by a nanomechanical sensor. In fact, the present inventors have found a receptor material for a nanomechanical sensor capable of reducing such a negative influence of water, and have succeeded in facilitating the detection of a trace component even when moisture is contained at a high ratio in a sample (Patent Literature 3).

On the other hand, the present inventors have made studies on selectivity for receptor materials for the nanomechanical sensor and a specimen for the purpose of increasing the sensitivity of the nanomechanical sensor, and have found a substance having particularly high selectivity for ammonia. In addition, the present inventors have found that when the substance is used as a material of a receptor layer, ammonia is detected with excellent sensitivity in a state in which a sample contains moisture, that is, in a humidified state, as compared with a state in which the sample does not contain moisture, and with high selectivity without adding another specimen selecting means such as a filter, and have completed the present invention based on these findings.

The present invention includes the following aspects.

(1) A method for detecting ammonia comprising supplying a sample gas to a nanomechanical sensor that detects a stress or a displacement using poly(methyl vinyl ether-alt-maleic anhydride) as a material of a receptor layer, the sample gas having a possibility to contain ammonia, and detecting presence or absence of ammonia or the content of ammonia in the sample gas based on an output signal from the nanomechanical sensor, in which the sample gas is a humidified sample gas with controlled relative humidity.

(2) The ammonia detection method according to (1), in which the humidified sample gas is obtained by adding water vapor to the sample gas.

(3) The ammonia detection method according to (1) or (2), in which the nanomechanical sensor is a surface stress sensor.

(4) The ammonia detection method according to (2) or (3), in which the water vapor is added by mixing a gas containing water vapor with the sample gas.

(5) The ammonia detection method according to any one of (1) to (4), in which the sample gas and a purge gas are alternately supplied to the nanomechanical sensor, and presence or absence of ammonia or the content of ammonia in the sample gas is detected based on the output signal obtained by the alternate supply.

(6) The ammonia detection method according to (5), in which the purge gas contains water vapor.

(7) The ammonia detection method according to (6), in which a relative humidity of the purge gas and a relative humidity of the sample gas are equal to each other.

(8) The ammonia detection method according to any one of (1) to (7), in which a relative humidity of the sample gas is 10% or more and 100% or less.

(9) A device for detecting ammonia comprising a gas path which a sample gas having a possibility to contain ammonia is introduced, a nanomechanical sensor that detects a stress or a displacement using poly(methyl vinyl ether-alt-maleic anhydride) as a receptor, and means for mixing water vapor with the sample gas, in which presence or absence of ammonia or the content of ammonia in the sample gas is detected according to the method for detecting ammonia according to any one of (1) to (8).

Advantageous Effects of Invention

According to the present invention, ammonia can be detected with high sensitivity and high selectivity with a simple sensor structure by using poly(methyl vinyl ether-alt-maleic anhydride) as a material of a receptor layer of a nanomechanical sensor and controlling a relative humidity of a sample gas. In addition, such highly sensitive ammonia detection can be achieved under the condition of supplying a sample gas at a low flow rate, which has not been verified before.

DESCRIPTION OF EMBODIMENTS

Figure 1:
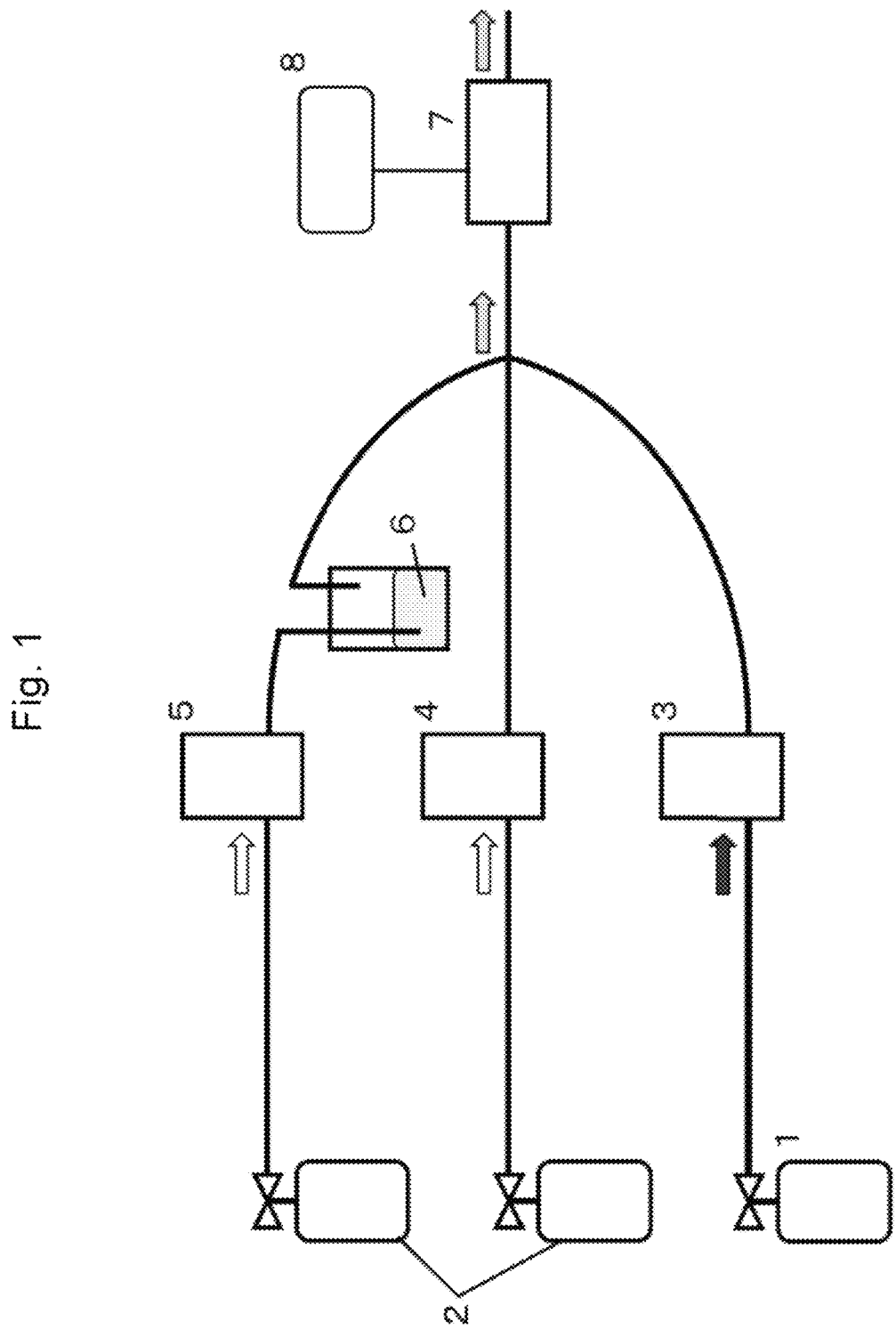
FIG. 1 is a conceptual illustration of a device configuration in which ammonia detection experiments were performed in Examples.

In a method for detecting ammonia according to an embodiment of the present invention, poly(methyl vinyl ether-alt-maleic anhydride) represented by the following chemical structural formula is used as a material of a receptor layer of a nanomechanical sensor.

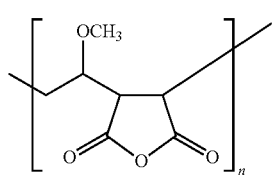

[Chemical Formula 1]

In the nanomechanical sensor (a sensor that does not resonate an element and operates in a so-called "static mode"), a sensor body detects a stress generated by adsorption or the like of a certain specimen molecule by a receptor layer or a displacement caused as a result of the stress. Therefore, the structure, operation, and the like of the sensor body usable in the present invention are not particularly limited as long as the sensor body detects a change in physical parameter caused in the sensor body by a stress generated in the receptor layer due to adsorption or the like of a specimen by the receptor layer coating a surface of the sensor body or a displacement caused by the stress. For example, when the nanomechanical sensor is a surface stress sensor, the surface stress sensor detects a change in stress caused in the receptor layer by adsorption or the like of a specimen by the receptor layer coating a surface of the sensor body and outputs a signal.

Examples of the nanomechanical sensor coated with a receptor include various surface stress sensors described in Patent Literature 1, but the shape, material, size, and the like thereof are not particularly limited, and any object can be used. For example, a thin-piece member supported at one or multiple positions can be preferably used. In addition, for example, it is possible to adopt various forms such as a thin-piece object or a membrane body supported at two or more positions such as a double-supported beam.

Furthermore, in addition to the surface stress sensor, although it is not necessarily possible to expect exactly the same effect depending on a difference in measurement principle, the effect of the present invention can be obtained by using poly(methyl vinyl ether-alt-maleic anhydride) as a material of a receptor layer, in another type of nanomechanical sensor that operates in a dynamic mode (mode of detecting a change in mass by resonating an element) such as a quartz crystal microbalance (QCM) and a sensor using a vibrator such as a cantilever; a sensor using surface plasmon resonance (SPR); a sensor that measures electrical conductivity of a material containing a conductive material such as metal nanoparticles or a material containing a conductive material such as carbon black; a field effect transistor and a sensor to which the principle of the field effect transistor is applied, or the like.

Note that, in the Examples described below, MSS is used as a nanomechanical sensor, but a nanomechanical sensor that can be used in the present invention is not intended to be limited thereto.

A method for coating a surface of a nanomechanical sensor body with a receptor to form a receptor layer is not particularly limited, and examples thereof include inkjet spotting, dip coating, spray coating, spin coating, casting, and coating using a doctor blade. Note that in Examples, an example in which a surface of the sensor body is directly coated with a material of a receptor is described, but there is no intention to exclude other forms. Other non-limiting examples include a coating via a self-assembled film, or a mixture with other components such as binders can be used as a receptor layer. Adhesion between a surface of the sensor body and a receptor material can be improved or enhanced by coating via a self-assembled film or coating with a mixture with other components such as binders.

In the present invention, "sample gas" is a gas possibly containing ammonia, and the origin of the gas is not limited. In a representative embodiment, the sample gas is a gas derived from an animal such as a human or livestock, and more specifically, exhaled breath or a skin gas derived from a human. In another embodiment, the sample gas may be an exhaust gas discharged from an engine (internal combustion engine) such as an automobile. In the present invention, by supplying a humidified sample gas in which the relative humidity of the sample gas is controlled to a nanomechanical sensor in which a surface of a sensor body is coated with poly(methyl vinyl ether-alt-maleic anhydride) as a material of a receptor layer, presence or absence of ammonia or the content of ammonia in the humidified sample gas is detected based on an output signal from the nanomechanical sensor. Note that in the present invention, "detection" of ammonia refers to at least one of detecting presence or absence of ammonia in a sample gas, and detecting or determining the content of ammonia in the sample gas.

In a preferred embodiment, by adding water vapor to a sample gas, a humidified sample gas in which the relative humidity of the sample gas is controlled is obtained. A method for adding water vapor to a sample gas is not particularly limited, but for example, water vapor can be added to a sample gas by mixing a gas containing water vapor with a sample gas. In this case, the relative humidity of the gas containing water vapor is not particularly limited, but may be, for example, 100% or any value less than 100%. In addition, the relative humidity of the humidified sample gas is preferably controlled to 10% or more and 100% or less.

In a preferred embodiment, a humidified sample gas and a purge gas are alternately supplied to a nanomechanical sensor in which a surface of a sensor body is coated with poly(methyl vinyl ether-alt-maleic anhydride) as a material of a receptor layer, and presence or absence of ammonia or the content of ammonia in the humidified sample gas is detected based on an output signal from the nanomechanical sensor obtained by the alternate supply. As a result, an influence caused by operation of a detection device or the like can be reduced, and the accuracy of an ammonia detection result can be further enhanced.

In the present invention, "purge gas" refers to a gas supplied for the purpose of cleaning a surface of a receptor layer with which the nanomechanical sensor body is coated. The composition of the purge gas is not particularly limited, but the purge gas preferably contains water vapor from a viewpoint of further enhancing the detection accuracy of ammonia in the humidified sample gas, and the relative humidity of the purge gas and the relative humidity of the humidified sample gas are more preferably the same as each other. By making the relative humidity of the purge gas and the relative humidity of the humidified sample gas the same as each other, an influence of components other than ammonia in a detection result of ammonia can be reduced, and analysis such as extraction of a feature value based on the detection result and detection of presence or absence of ammonia and/or the content of ammonia can be performed more simply and quickly.

A device for detecting ammonia according to an embodiment of the present invention comprises a gas path which a sample gas possibly containing ammonia is introduced, a nanomechanical sensor that detects a stress or a displacement using poly(methyl vinyl ether-alt-maleic anhydride) as a receptor, and a mixing means for mixing water vapor with the sample gas, and detects presence or absence of ammonia or the content of ammonia in the sample gas according to the above-described method for detecting ammonia.

In a preferred embodiment, the ammonia detection device comprises a gas path which a purge gas is introduced.

In a preferred embodiment, the ammonia detection device comprises a means for measuring the relative humidity of a sample gas and/or a purge gas. The relative humidity of each of the sample gas and the purge gas may be measured by a relative humidity measurement means disposed in the ammonia detection device. Alternatively, a purge gas with adjusted relative humidity may be supplied to the nanomechanical sensor by measuring in advance the relative humidity of a humidified sample gas with controlled relative humidity before being supplied to the nanomechanical sensor. In this case, the relative humidity of the purge gas can be controlled by adding water vapor to the purge gas, and a means for adding water vapor to the purge gas can be disposed in the ammonia detection device.

Note that in the present invention, it is advantageous that the relative humidity of the purge gas and the relative humidity of the humidified sample gas are equal to each other because controlling of the amount of the water vapor addition during measurement and the structure of the measurement device are simplified (especially when the sample gas is dry or contains only a little amount of water vapor), the number of parameters of measurement conditions is reduced and so on. Furthermore, even if ammonia detection sensitivity changes sensitively with respect to a slight difference between the relative humidity of the purge gas and the relative humidity of the humidified sample gas (for example, 1%, although not limited thereto), and such a difference gives a change in detection signal larger than presence or absence of ammonia, such a change can be compensated for by measurement in advance or other methods. Therefore, it is a matter of course that a condition such as making the relative humidity of the purge gas and the relative humidity of the humidified sample gas the same as each other or fixing a difference between the relative humidity of the purge gas and the relative humidity of the humidified sample gas to a specific value is not essential to the present invention.

EXAMPLES

Hereinafter, the present invention will be described in more detail with reference to Examples. It is to be understood that the following Examples are intended to aid in understanding of the present invention and are not intended to limit the present invention to the following Examples at all.

Example 1

In this Example, a MSS (i.e., a piezoresistive type surface stress sensor having a membrane type structure) was used as a nanomechanical sensor. Since the structure, operation, and other features of MSS are well known to those skilled in the art, further description is omitted, but refer to Patent Literature 1, Non Patent Literature 1, and the like as necessary. Note that MSS used here had a membrane (a disk-shaped thin membrane part to which a receptor layer is coated, the thin membrane part being supported by a peripheral frame part with a narrow width part in which a piezoresistive element is embedded) having a diameter of 300 μm and a thickness of 5 μm.

Poly(methyl vinyl ether-alt-maleic anhydride) (product number 416320) obtained from Sigma-Aldrich Japan was dissolved in N,N-dimethylformamide to prepare a 1 g/L solution, and then the solution was coated on an MSS body (sensor chip) by an inkjet spotter so as to have a thickness of about 1 μm. At this time, the sensor chip was heated to 80° C. in order to accelerate drying of the coating liquid.

FIG. 1 is a conceptual illustration of a device configuration in which ammonia detection experiments were performed in this Example. In FIG. 1, ammonia as a specimen is introduced from a mass flow controller 3 (MFC1) to which an ammonia standard gas cylinder 1 (ammonia concentration: 100 ppm, nitrogen balance) is connected via a gas path into a sensor chamber (sealed chamber) 7 storing MSS having a receptor layer coated with poly(methyl vinyl ether-alt-maleic anhydride). Gas paths from two mass flow controllers 4 and 5 (MFC2 and MFC3) connected to two nitrogen gas cylinders 2 merge with a gas path from the mass flow controller 3 (MFC1) in front of (upstream of) a gas supply port to the sensor chamber 7 to form a mixed gas, and the mixed gas is introduced into the sensor chamber 7. A container containing water 6 is disposed downstream of the mass flow controller 5 (MFC 3), and the water 6 is bubbled with a nitrogen gas to obtain a humidified nitrogen gas having a relative humidity of 100%. The humidified nitrogen gas merges with gas paths from the mass flow controller 4 (MFC 2) and the mass flow controller 3 (MFC 1). An output signal from MSS stored in the sensor chamber 7 is read by a personal computer (measurement terminal) 8 connected to the sensor chamber 7, and ammonia is detected. Note that in FIG. 1, an arrow schematically indicates a direction in which a gas flows. An ammonia gas (black arrow) supplied from the ammonia standard gas cylinder 1 to the mass flow controller 3 (MFC1) is mixed with nitrogen gases (white arrows) supplied from the two nitrogen gas cylinders 2 to the two mass flow controllers 4 and 5 (MFC2 and MFC3) to form a mixed gas (gray arrow). The mixed gas (gray arrow) is introduced into the sensor chamber 7 and then discharged from a gas discharge port of the sensor chamber 7 to the outside of the chamber.

Using such an experimental device, operation of switching between "injection" in which a sample gas containing ammonia gas was supplied to the sensor chamber 7 and "purge" in which a nitrogen gas (purge gas) not containing an ammonia gas was supplied to the sensor chamber 7 to clean a receptor layer of a sensor body at intervals of five minutes was performed for four cycles in total, and ammonia was detected.

A ratio between the flow rate of the mass flow controller 3 (MFC 1) and the total flow rate of the mass flow controllers 4 and 5 (MFC2 and MFC3) was adjusted to be 1:1, and an ammonia concentration in the sample gas was set to 50 ppm.

As shown in Table 1 below, the flow rates of the mass flow controllers 3, 4, and 5 (MFC1, MFC2, and MFC3) were controlled, and a relative humidity (RH) of each of the sample gas and the purge gas in the injection and the purge was set to three conditions of 0%, 25%, and 50%. Under any of the relative humidity conditions, the total flow rate of the mass flow controllers 3, 4, and 5 (MFC1, MFC2, and MFC3) in the injection and the purge was set to 30 sccm.

TABLE 1

| | Injection | Purge |
|---|---|---|
| Relative Humidity 0%, Ammonia Concentration 50 ppm | | |
| MFC1 | 15 | 0 |
| MFC2 | 15 | 30 |
| MFC3 | 0 | 0 |
| Relative Humidity 25%, Ammonia Concentration 50 ppm | | |
| MFC1 | 15 | 0 |
| MFC2 | 7.5 | 22.5 |
| MFC3 | 7.5 | 7.5 |
| Relative Humidity 50%, Ammonia Concentration 50 ppm | | |
| MFC1 | 15 | 0 |
| MFC2 | 0 | 15 |
| MFC3 | 15 | 15 |

Unit : sccm

Figure 2:
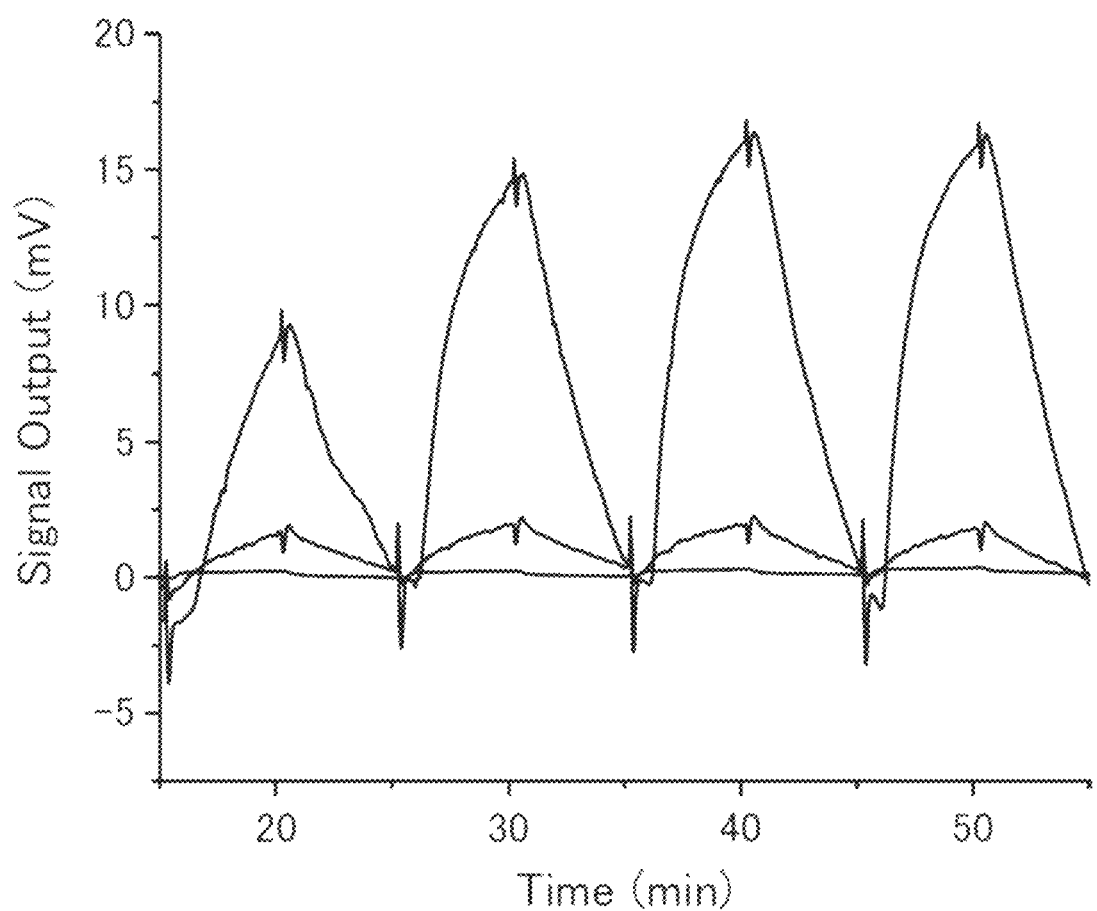
FIG. 2 is a graph showing results of ammonia detection experiments using a sample gas containing ammonia having a concentration of 50 ppm under a condition where relative humidity (RH) of each of the sample gas and a purge gas was 0%, 25%, or 50% (Example 1).

The results are shown in FIG. 2. In FIG. 2, the horizontal axis represents time (minutes) from start of the experiment, and the vertical axis represents signal output (mV) from MSS. In this regard, processing was performed such that a baseline of a signal was 0 mV by subtracting an offset of each signal. In addition, 15 minutes from start of the experiment is a preparation time for securing stability of operation of MSS, and therefore measurement results of the output signal during this period are omitted. The same applies to FIGS. 3 and 4 described later.

As shown in FIG. 2, under a condition that the relative humidity of each of the sample gas and the purge gas was 0%, an output signal from MSS was hardly confirmed in each of the injection operation and the purge operation, but under a humidification condition that the relative humidity of each of the sample gas and the purge gas was 25% or 50%, output signals from MSS were clearly confirmed. Specifically, when the injection was started at a time point of 15 minutes, an output signal intensity increased, and when the operation was switched to the purge at a time point of 20 minutes, a spike caused by the switching operation occurred, and then the output signal intensity decreased. In addition, when the operation was switched to the injection again at a time point of 25 minutes, the output signal intensity increased again, and thereafter, signal waveforms with high reproducibility were obtained in response to an injection/purge switching operation. Furthermore, when the relative humidity was 50%, very large output signals were generated from MSS as compared with a case where the relative humidity was 25%, and a signal intensity of about 15 mV was obtained.

If it is assumed that a noise level of MSS is 0.01 my, limit of detection is S/N=3, and a sensor response intensity is proportional to a specimen concentration based on findings obtained by the present inventors by performing measurements for various chemical substances using MSS coated with various receptor materials, these results indicate that ammonia in an extremely low concentration region of 0.1 ppm in terms of calculation can be detected. Moreover, the flow rate of the sample gas in the experiment on which this calculation is based (strictly, the total flow rate of the sample gas supplied to the sensor after addition of water vapor for humidification) is 30 sccm, which is a low flow rate that has not been verified before in detection of ammonia having a low concentration.

In addition, since the signal waveforms have high stability, it is considered that by supplying a sample gas possibly containing ammonia to a nanomechanical sensor having a configuration equivalent to that of this Example and analyzing an obtained signal intensity and signal waveforms, it is possible to identify that ammonia is contained.

Comparative Example 1

Using an experimental device having a configuration similar to that of Example 1, detection of trimethylamine by MSS having a receptor layer coated with poly(methyl vinyl ether-alt-maleic anhydride) was attempted using a trimethylamine gas, which is also a nitrogen-containing compound, instead of an ammonia gas. Note that a trimethylamine concentration in the sample gas was set to 50 ppm, and as in Example 1, by mixing a trimethylamine gas and a nitrogen gas under predetermined conditions, the relative humidity of each of the sample gas and the purge gas was set to three conditions of 0%, 25%, and 50%.

Figure 3:
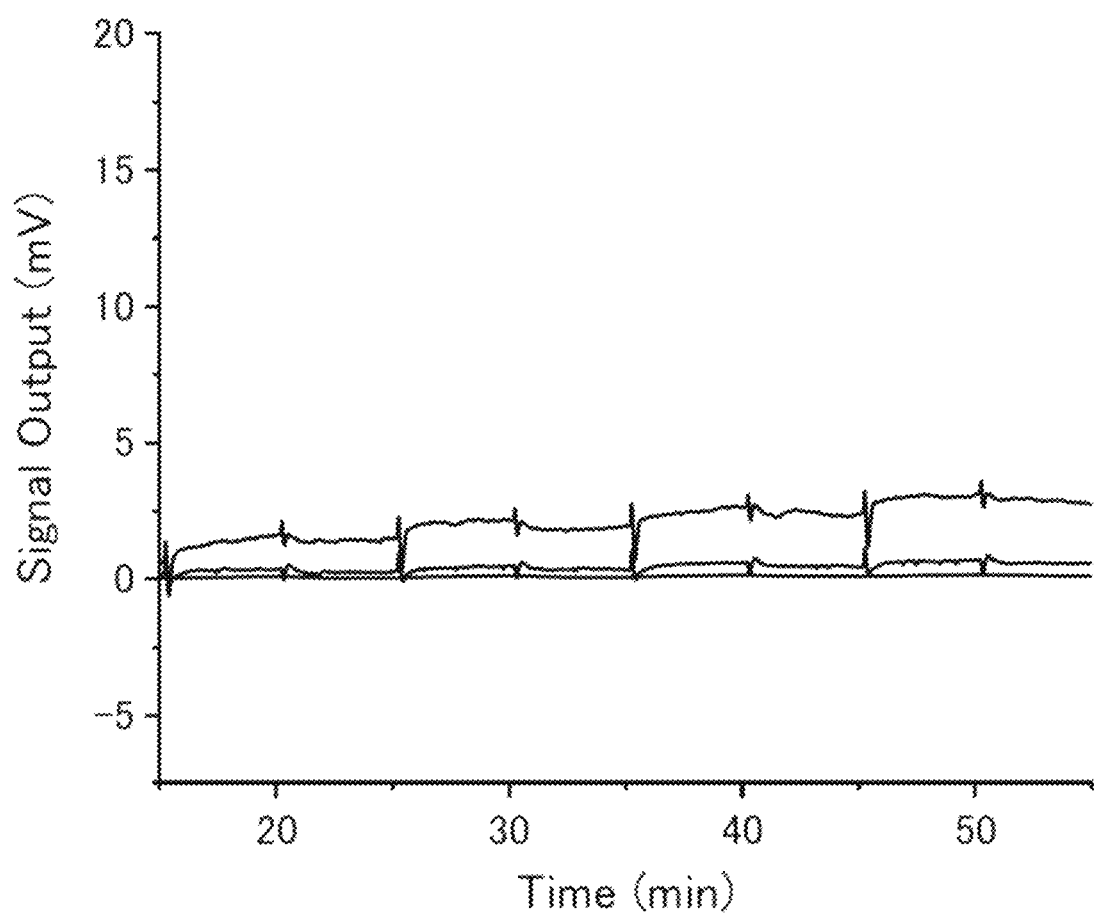
FIG. 3 is a graph showing results of trimethylamine detection experiments using a sample gas containing trimethylamine having a concentration of 50 ppm under a condition where relative humidity (RH) of each of the sample gas and a purge gas was 0%, 25%, or 50% (Comparative Example 1).

The results are shown in FIG. 3.

As shown in FIG. 3, as the relative humidity of each of the sample gas and the purge gas was increased in order of 0%, 25%, and 50%, output signals from MSS increased slightly, but a significant increase in signal intensity as obtained in Example 1 was not confirmed.

In addition, when a spike portion at the time of switching from the injection to the purge was excluded, commonality was not recognized in signal waveforms obtained by switching between the injection and the purge four times in total. Therefore, it is not possible to extract any feature value from the signal intensity and the signal waveforms, and it is considered that it is almost impossible to identify whether the sample gas contains a specimen (in this case, triethylamine).

Therefore, from these results, it has been found that, in MSS having poly(methyl vinyl ether-alt-maleic anhydride) as a receptor layer, unlike the sensor disclosed in Patent Literature 2 that requires a filter that selects only ammonia among many kinds of gases to which a material of the sensor responds, MSS itself having the receptor layer has extremely high selectivity to ammonia even if MSS is brought into direct contact with the sample gas, and such high selectivity is indicated as signal waveforms having high signal intensity and excellent stability by using a humidified sample gas with controlled relative humidity.

Note that although results are not shown in the figures, even when similar experiments were performed using a plurality of substances other than trimethylamine, any of output signals from MSS in which it was recognized that a specimen could be detected, a remarkable increase in signal intensity under a humidified condition, and stable signal waveforms, as obtained in Example 1, was not confirmed. In addition, since similar results were obtained in the same measurements performed by changing the date and time, it can be said that ammonia detection in MSS having poly (methyl vinyl ether-alt-maleic anhydride) as a receptor layer has high reproducibility.

Example 2

Next, using an experimental device having a configuration similar to that of Example 1, trimethylamine was detected by MSS having a receptor layer coated with poly (methyl vinyl ether-alt-maleic anhydride) by setting the relative humidity of each of the sample gas and the purge gas to 50% and setting the ammonia concentration in the sample gas to three conditions of 50 ppm, 30 ppm, and 10 ppm. Note that the flow rates of the mass flow controllers 3, 4, and 5 (MFC1, MFC2, and MFC3) when the ammonia concentration was set to 30 ppm or 10 ppm were controlled as shown in Table 2 below, and the total flow rate of the mass flow controllers 3, 4, and 5 (MFC1, MFC2, and MFC3) in the injection and the purge was set to 30 sccm.

TABLE 2

|  | Injection | Purge |
| --- | --- | --- |
| Relative Humidity 50%, Ammonia Concentration 30 ppm | | |
| MFC1 | 9 | 0 |
| MFC2 | 6 | 15 |
| MFC3 | 15 | 15 |
| Relative Humidity 50%, Ammonia Concentration 10 ppm | | |
| MFC1 | 3 | 0 |
| MFC2 | 12 | 15 |
| MFC3 | 15 | 15 |

Unit : sccm

Figure 4:
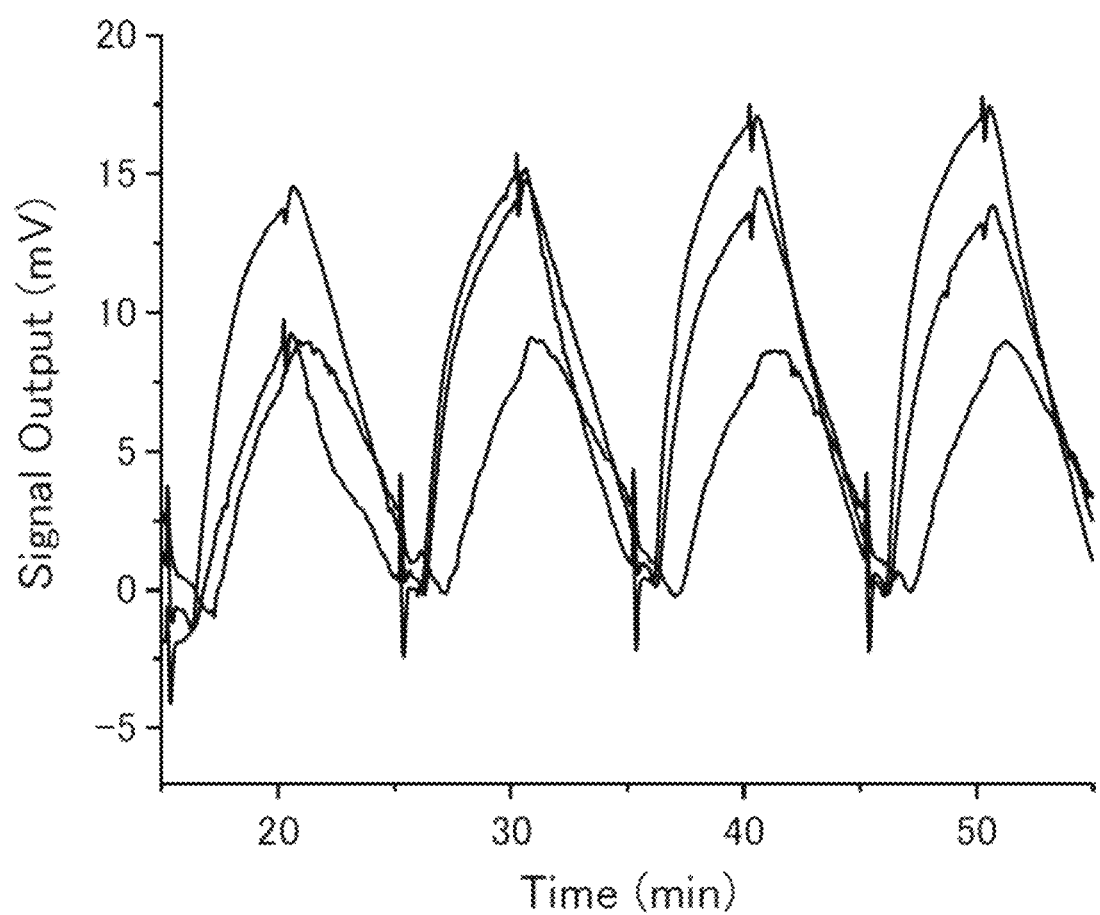
FIG. 4 is a graph showing results of ammonia detection experiments using a sample gas having a relative humidity of 50% under a condition where an ammonia concentration in the sample gas was 50 ppm, 30 ppm, or 10 ppm (Example 2).

The results are shown in FIG. 4.

As shown in FIG. 4, output signals from MSS decreased as the ammonia concentration in the sample gas decreased in order of 50 ppm, 30 ppm, and 10 ppm. Note that as the concentration decreased, signal responses shifted to the right as a whole; however, this is because a delay occurs in supply and interruption of the ammonia gas in a pipe due to a decrease in flow rate of the MFC1, and this is not an essential problem. Rather, surprisingly, with respect to a signal intensity of about 17 mV obtained when the ammonia concentration was 50 ppm, a signal intensity of about 15 mV was obtained when the concentration was 30 ppm, which is ⅗ of 50 ppm, and a signal intensity of 9 mV was obtained when the ammonia concentration was 10 ppm, which is ⅕ of 50 ppm. That is, these results indicate that signal intensities higher than 17÷5×3=10.2 mV and 17÷5=3.4 mV, which are signal intensities expected when the intensity of a sensor response was assumed to be proportional to a specimen concentration from the signal intensity (about 17 mV) when the ammonia concentration was 50 ppm, were obtained.

Therefore, it has been suggested that ammonia detection by MSS having a receptor layer coated with poly(methyl vinyl ether-alt-maleic anhydride) was possible even in a concentration region lower than the calculated detectable concentration of 0.1 ppm estimated from the results of Example 1 even under supply of the sample gas at a low flow rate as described above.

The embodiments of the present invention have been described in detail above, but the specific form is not limited to the above embodiments, and modification and the like without departing from the gist of the present invention are also included in the present invention.

INDUSTRIAL APPLICABILITY

According to the present invention, it has been specifically demonstrated by the above Examples using MSS that ammonia in a humidified sample gas with controlled relative humidity can be accurately detected with high selectivity by a nanomechanical sensor having poly(methyl vinyl ether-alt-maleic anhydride) as a receptor layer, contrary to the conventional consideration that it is difficult to detect a trace amount of a specimen when moisture is contained in a sample. Since it has been indicated that ammonia can be detected even in a concentration region of 0.1 ppm or less, there is a possibility of wide use in industry, for example, an ammonia concentration in a skin gas or exhaled breath can be measured with high sensitivity and high accuracy.

The invention claimed is:

1. A method for detecting ammonia comprising
supplying a sample gas to a nanomechanical sensor that detects a stress or a displacement using poly(methyl vinyl ether-alt-maleic anhydride) as a material of a receptor layer, the sample gas having a possibility to contain ammonia, and
detecting presence or absence of ammonia or a content of ammonia in the sample gas based on an output signal from the nanomechanical sensor,
wherein the sample gas is a humidified sample gas with controlled relative humidity, the humidified sample gas being obtained by adding water vapor to the sample gas such that the relative humidity of the sample gas is 25% or more and 50% or less.

2. The ammonia detection method according to claim 1, wherein the nanomechanical sensor is a surface stress sensor.

3. The ammonia detection method according to claim 1, wherein the water vapor is added by mixing a gas containing water vapor with the sample gas.

4. The ammonia detection method according to claim 1, wherein
the sample gas and a purge gas are alternately supplied to the nanomechanical sensor, and
presence or absence of ammonia or a content of ammonia in the sample gas is detected based on the output signal obtained by the alternate supply.

5. The ammonia detection method according to claim 4, wherein the purge gas contains water vapor.

6. The ammonia detection method according to claim 5, wherein a relative humidity of the purge gas and a relative humidity of the sample gas are equal to each other.

7. A device for detecting ammonia comprising
a gas path which a sample gas having a possibility to contain ammonia is introduced,
a nanomechanical sensor that detects a stress or a displacement using poly(methyl vinyl ether-alt-maleic anhydride) as a receptor, and
a humidified gas path that merges with the gas path such that water vapor mixes with the sample gas so that the relative humidity of the sample gas is 25% or more and 50% or less,
wherein presence or absence of ammonia or a content of ammonia in the sample gas is detected according to the method for detecting ammonia according to claim 1.

* * * * *